(12) United States Patent
Sakurai et al.

(10) Patent No.: US 11,077,157 B2
(45) Date of Patent: Aug. 3, 2021

(54) MEDICINAL COMPOSITION FOR TREATING FIBROSIS

(71) Applicant: Osaka University, Suita (JP)

(72) Inventors: Fuminori Sakurai, Suita (JP); Hiroyuki Mizuguchi, Suita (JP)

(73) Assignee: Osaka University, Osaka (JP)

( * ) Notice: Subject to any disclaimer, the term of this patent is extended or adjusted under 35 U.S.C. 154(b) by 107 days.

(21) Appl. No.: 16/077,840

(22) PCT Filed: Feb. 15, 2017

(86) PCT No.: PCT/JP2017/005443
§ 371 (c)(1),
(2) Date: Aug. 14, 2018

(87) PCT Pub. No.: WO2017/141942
PCT Pub. Date: Aug. 24, 2017

(65) Prior Publication Data
US 2019/0151384 A1    May 23, 2019

(30) Foreign Application Priority Data

Feb. 16, 2016 (JP) .............................. JP2016-027202

(51) Int. Cl.
| | | |
|---|---|---|
| *A61K 35/765* | (2015.01) | |
| *A61P 9/10* | (2006.01) | |
| *A61P 1/16* | (2006.01) | |
| *A61P 13/12* | (2006.01) | |
| *A61P 11/00* | (2006.01) | |
| *A61P 29/00* | (2006.01) | |
| *A61K 9/00* | (2006.01) | |
| *C12N 7/00* | (2006.01) | |

(52) U.S. Cl.
CPC .......... *A61K 35/765* (2013.01); *A61K 9/0019* (2013.01); *A61P 1/16* (2018.01); *A61P 9/10* (2018.01); *A61P 11/00* (2018.01); *A61P 13/12* (2018.01); *A61P 29/00* (2018.01); *C12N 7/00* (2013.01)

(58) Field of Classification Search
None
See application file for complete search history.

(56) References Cited

U.S. PATENT DOCUMENTS

| | | |
|---|---|---|
| 5,525,342 A | 6/1996 | Rosenberger et al. |
| 6,632,647 B2 | 10/2003 | Hirth-Dietrich et al. |
| 8,470,312 B2 | 6/2013 | Coffey et al. |
| 9,309,203 B2 | 4/2016 | Wikel et al. |
| 9,738,614 B2 | 8/2017 | Wikel et al. |
| 2002/0076418 A1 | 6/2002 | Hirth-Dietrich et al. |
| 2004/0091458 A1 | 5/2004 | Morris et al. |
| 2008/0081032 A1 | 4/2008 | Morris et al. |
| 2009/0104162 A1 | 4/2009 | Kim et al. |
| 2011/0070200 A1 | 3/2011 | Coffey et al. |
| 2013/0243732 A1 | 9/2013 | Coffey et al. |
| 2014/0249163 A1 | 9/2014 | Wikel et al. |
| 2016/0207891 A1 | 7/2016 | Wikel et al. |

FOREIGN PATENT DOCUMENTS

| | | |
|---|---|---|
| CN | 102065873 A | 5/2011 |
| CN | 103906518 A | 7/2014 |
| JP | H07-322877 A | 12/1995 |
| JP | 2004-502741 A | 1/2004 |
| JP | 2005-526124 A | 9/2005 |
| JP | 2014-196329 A | 10/2014 |
| WO | 00/50051 A2 | 8/2000 |
| WO | 2008/044627 A1 | 4/2008 |
| WO | 2008/110004 A1 | 9/2008 |
| WO | 2008/141448 A1 | 11/2008 |
| WO | 2012/045473 A1 | 4/2012 |

OTHER PUBLICATIONS

Majeski et al., Am J Pathol. Oct. 2003; 163(4): 1467-79 (Year: 2003).*
Phillips et al., Experimental Biology and Medicine 2013; 238: 461-481 (Year: 2013).*
Gosh et al., Experimental Biology and Medicine 2013; 238:461-481 (Year: 2013).*
Rosa et al. Nature- Scientific Reports (2019) 9:18599) (Year: 2019).*
Kim et al., J Am Soc Nephrol 12: 736-748 (Year: 2001).*
Extended European Search Report issued in corresponding European Patent Application No. 17753198.5 dated Sep. 7, 2019.
Li et al., Newcastle disease virus represses the activation of human hepatic stellate cells and reversed the development of hepatic fibrosis in mice, Liver International, 29: 593-602 (2009).
Lv et al., "Role of non-classical renin-angiotensin system axis in renal fibrosis," Frontiers in Physiology, 6: 1-8 (2005).
Grace et al., "Update on new aspects of the renin-angiotensin system in liver disease: clinical implications and new terapeutic options," Clinical Science, 123: 225-239 (2012).
Kaminade et al., "Reovirus-mediated lysis of cancer-associated fibroblasts," The 21st Annual Meeting of Japan Society of Gene Therapy Program and Abstracts, 238 (2015).
Kaminade et al., "An investigation of the apoptotic effect of oncolytic reovirus on malignancy-associated fibroblasts," DVD Abstract of the 135th Annual Meeting of the Pharmaceutical Society of Japan (2015) (see ISR/IPRP).
Vliyamoto et al., "Cardiac Cell-specific Apoptotic and Cytokine Responses to Reovirus Infection: Determinants of Myocarditic Phenotype," Journal of Cardiac Failure, 15: 529-539 (2009).

(Continued)

*Primary Examiner* — Shanon A. Foley
*Assistant Examiner* — Myron G Hill
(74) *Attorney, Agent, or Firm* — Morgan, Lewis & Bockius LLP

(57) ABSTRACT

The disclosure provides a pharmaceutical composition for use in treating fibrosis comprising a reovirus as an active ingredient.

17 Claims, 5 Drawing Sheets

(56) References Cited

OTHER PUBLICATIONS

International Search Report issued in corresponding International Patent Application No. PCT/JP2017/005443 dated Apr. 4, 2017.
International Preliminary Report on Patentability issued in corresponding International Patent Application No. PCT/JP2017/005443 dated Aug. 18, 2018.
Kaminade et al., "An investigation of the apoptotic effect of oncolytic reovirus on malignancy-associated fibroblasts," DVD Abstract of the 135th Annual Meeting of the Pharmaceutical Society of Japan (2015) (English translation of previously cited document).
Office Action issued in corresponding Japanese Patent Application No. 2018-500140 dated Dec. 8, 2020.
Office Action issued in corresponding Chinese Patent Application No. 201780023781.8 dated Jun. 2, 2021.

* cited by examiner

MEDICINAL COMPOSITION FOR TREATING FIBROSIS

TECHNICAL FIELD

This patent application claims priority to Japanese patent application No. 2016-27202, the whole of which is incorporated herein by reference.

The present disclosure relates to pharmaceutical compositions for use in treating fibrosis.

BACKGROUND

Tissue fibrosis occurs in various organs, such as liver and kidney, and causes organ failure and many diseases including tumors. Although various kinds of therapeutic agents for fibrosis have been developed, their therapeutic effects are not sufficient. Thus, there has been a need for new therapeutic agents.

Reovirus is an RNA virus that has double-stranded RNA genome. The reovirus is known as an oncolytic virus. The reovirus fails to infect normal cells but infects cancer cells with high efficiency to kill the cells, and has been in clinical development as an anticancer agent. The present inventors have reported that reovirus has a high cytocidal effect on cancer-associated fibroblasts, which are localized in cancer tissues. The effects of reovirus on tissue fibrosis, however, have not been reported.

CITATION LIST

Patent Documents

Patent document 1: WO 00/50051
Patent document 2: WO 2008/141448
Patent document 3: WO 2008/110004

Non Patent Documents

Non-patent document 1: The 21th Annual Meeting of Japan Society of Gene Therapy Program and Abstracts. Japan Society Gene Therapy, Japan Society Gene Therapy, JSGT p238, Jul. 10, 2015

SUMMARY

An object of the present disclosure is to provide a therapeutic agent for tissue fibrosis, which has been reported in many diseases.

The present disclosure provides a pharmaceutical composition for use in treating fibrosis comprising a reovirus as an active ingredient.

Provided is a therapeutic agent for tissue fibrosis having excellent therapeutic effects.

DESCRIPTION OF EMBODIMENTS

Figure 1:
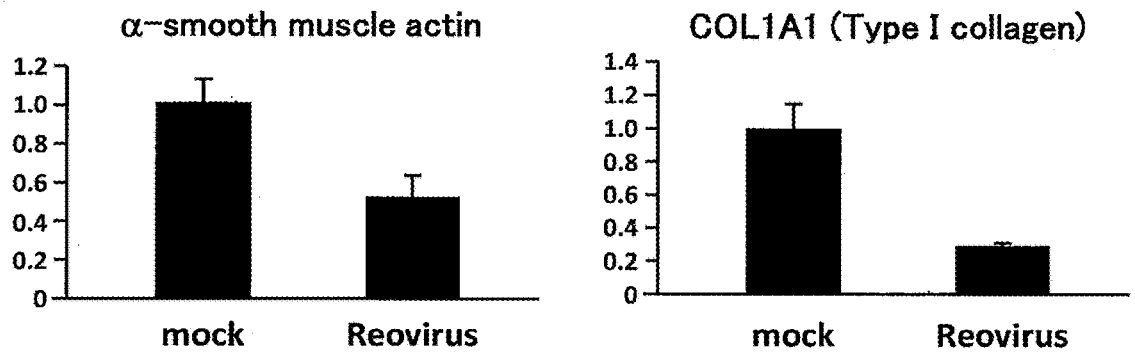
FIG. 1 shows expression of fibrosis markers in activated human hepatic stellate cells (LX-2).

As used herein, the term "reovirus" means mammalian orthoreovirus. The mammalian orthoreovirus is a reovirus whose host is a mammal such as human. Mammalian orthoreovirus includes three serotypes of type 1 (strain Lang, also referred to as T1L), type 2 (strain Jones, also referred to as T2J), and type 3 (strain Dearing or strain Abney, also referred to as T3D or T3A). In a preferred embodiment, the reovirus is a strain of mammalian orthoreovirus type 3. In a more preferred embodiment, the reovirus is strain Dearing of mammalian orthoreovirus type 3.

The reovirus as used herein may be a reovirus that receives a treatment to improve the efficiency of entry into cells or to lower its immunogenicity. For example, the reovirus may be a reovirus treated with a protease (such as chymotrypsin or trypsin) to remove a part of capsids and enhance the efficiency of cellular uptake. The reovirus may also be a reovirus that forms a complex with, or is encapsulated in, a liposome or a polymer particle to reduce or avoid immune responses in a subject who receives the reovirus.

The reovirus may be a naturally-occurring wild-type or mutated virus, or may be a recombinant virus that is modified for any of various purposes, such as improving the efficiency of entry into cells, lowering immunogenicity, and reducing toxicity. Examples of recombinant reoviruses include a reovirus having a mutation(s) in a capsid protein(s) such as σ3, μ1, or λ2 (WO2008/141448, WO2008/110004).

The reovirus may be a reovirus obtained by gene reassortment of two or more genetically different reoviruses. The gene reassortment may occur when at least two genetically different reoviruses co-infect a single host cell. Such a reovirus may be prepared by co-infection of genetically different reoviruses in a host cell.

The reovirus may be an alive virus (i.e., a virus having infectious ability), or an inactivated virus (i.e., a virus not having infectious ability). The phrase "having infectious ability" means that the reovirus has the abilities to enter into cells and to self-replicate in the cells. Thus, the inactivated virus includes a virus having the ability to enter into cells but not having the ability to self-replicate in the cells, and a virus not having both abilities. Examples of such inactivated viruses include a virus inactivated by degradation of genomic RNA by UV irradiation, and a virus inactivated by radiation. When the inactivated virus lacks the ability to enter into cells, the virus may be encapsulated into a liposome or a polymer particle to be delivered into cells.

Fibrosis is a phenomenon in which fibroblasts in a tissue are activated and produce a large amount of extracellular matrix components such as type I collagen to cause abnormal growth of connective tissue. As used herein, treatment of fibrosis includes reduction or removal of a fibrotic tissue, suppression of fibrosis progression, and maintenance of an improved fibrotic tissue.

The pharmaceutical composition of the disclosure is effective for treating a disease accompanied by tissue fibrosis. As tissue fibrosis has been reported to occur in a variety of organs, including liver, lung, bone marrow, intestine, heart, kidney and skin, the pharmaceutical composition of the disclosure may be used to treat fibrosis in such organs. In one embodiment, the pharmaceutical composition of the disclosure is used to treat fibrosis in liver or lung. Diseases and conditions that may be treated with the pharmaceutical composition of the disclosure include liver fibrosis, liver cirrhosis, hepatitis B, hepatitis c, alcoholic hepatitis, non-alcoholic steatohepatitis, pulmonary fibrosis (for example, idiopathic pulmonary fibrosis or pulmonary fibrosis associated with a disease such as collagen disease or sarcoidosis), bone marrow fibrosis (for example, idiopathic myelofibrosis or bone marrow fibrosis associated with a disease such as collagen disease or blood tumor), fibrosis of the intestinal tract associated with inflammatory bowel disease, cardiac fibrosis associated with myocardial infarction, renal fibrosis associated with chronic renal disease, and skin fibrosis such as scleroderma. In one embodiment, the pharmaceutical composition of the disclosure is used to treat liver fibrosis, liver cirrhosis, hepatitis B, hepatitis c, alcoholic hepatitis, non-alcoholic steatohepatitis, or pulmonary fibrosis, preferably liver fibrosis or pulmonary fibrosis. In another embodiment, the pharmaceutical composition of the disclosure is used to treat cardiac fibrosis associated with myocardial infarction. In another embodiment, the pharmaceutical composition of the disclosure is used to treat skin fibrosis such as scleroderma. The pharmaceutical composition of the disclosure may be used in combination with other therapeutic agents for fibrosis.

The pharmaceutical composition may comprise a pharmaceutically acceptable carrier in addition to the reovirus as an active ingredient. Examples of pharmaceutically acceptable carriers include phosphate buffered saline or other physiologically acceptable buffer, lactose, dextrose, sucrose, sorbitol, mannitol, starch, gum arabic, calcium phosphate, alginate, tragacanth, gelatin, calcium silicate, microcrystalline cellulose, polyvinyl pyrrolidone, cellulose, sterile water, syrup, and methylcellulose. The pharmaceutical composition may further comprise an additive such as a smoothing agent (such as talc, magnesium stearate, or mineral oil), a wetting agent, an emulsifier, a suspending agent, a preservative (such as methyl benzoate or propylhexedrine benzoate), a sweetener, and a flavor. The pharmaceutical composition may be formulated by any of conventional methods in the art.

The pharmaceutical composition may be administered by oral administration or by parenteral administration (such as intravenous, intramuscular, subcutaneous, transdermal, nasal, or pulmonary administration). The pharmaceutical composition may be administered by systemic administration or local administration. In one embodiment, the pharmaceutical composition is administered by oral administration, intravenous administration, or pulmonary administration, preferably by intravenous administration. Intravenous administration may be performed by injection or infusion.

The pharmaceutical composition may be, but not limited to, in the form of tablets, pills, capsules, granules, powders, oral solutions (such as elixirs, suspensions, and emulsions), syrups, inhalants, suppositories, injections, and patches. The injections include injectable solutions and solid injectable forms to be reconstituted prior to use (for example, a lyophilized product for injection).

The dosage of the reovirus may be appropriately determined based on factors such as the virus to be used, age, sex, weight, or severity of disease of the subject to be treated, or the dosage form, and may be about 1 PFU (plaque forming unit) to about $10^{17}$ PFU, about 10 PFU to $10^{15}$ PFU, or about $10^2$ PFU to $10^{13}$ PFU per kg body weight. The dosage per treatment may be administered at one time, or divided and administered at multiple times (such as at two, three, four or more times). The treatment with the reovirus may be continued for several days, weeks, months, or more.

The disclosure also provides a method for treating fibrosis, comprising administering a reovirus to a subject, and use of a reovirus for manufacturing a medicament for the treatment of fibrosis. The method and use may be carried out in accordance with the descriptions for the pharmaceutical composition of the disclosure.

The present disclosure provides, for example, the following embodiments.

1. A pharmaceutical composition for use in treating fibrosis comprising a reovirus as an active ingredient.
2. The pharmaceutical composition for use according to item 1, wherein the reovirus is a strain of mammalian orthoreovirus type 3.
3. The pharmaceutical composition for use according to item 1 or 2, wherein the reovirus is strain Dearing of mammalian orthoreovirus type 3.
4. The pharmaceutical composition for use according to any one of items 1-3, wherein the reovirus is an alive virus.
5. The pharmaceutical composition for use according to any one of items 1-3, wherein the reovirus is an inactivated virus.
6. The pharmaceutical composition for use according to any one of items 1-5, wherein the pharmaceutical composition is for use in treating fibrosis in an organ selected from liver, lung, bone marrow, intestine, heart, and kidney.
7. The pharmaceutical composition for use according to item 6, wherein the pharmaceutical composition is for use in treating fibrosis in liver, lung, or heart.
8. The pharmaceutical composition for use according to item 6 or 7, wherein the pharmaceutical composition is for use in treating fibrosis in liver or lung.
9. The pharmaceutical composition for use according to any one of items 1-5, wherein the pharmaceutical composition is for use in treating a disease or a condition selected from liver fibrosis, liver cirrhosis, hepatitis B, hepatitis c, alcoholic hepatitis, non-alcoholic steatohepatitis, pulmonary fibrosis, bone marrow fibrosis, fibrosis of the intestinal tract associated with inflammatory bowel disease, cardiac fibrosis associated with myocardial infarction, and renal fibrosis associated with chronic renal disease.
10. The pharmaceutical composition for use according to item 9, wherein the pharmaceutical composition is for use in treating liver fibrosis, liver cirrhosis, hepatitis B, hepatitis c, alcoholic hepatitis, non-alcoholic steatohepatitis, or pulmonary fibrosis.
11. The pharmaceutical composition for use according to any one of items 1-5, wherein the pharmaceutical composition is for use in treating cardiac fibrosis associated with myocardial infarction.
12. The pharmaceutical composition according to any one of items 1-5, wherein the pharmaceutical composition is for use in treating skin fibrosis.
13. The pharmaceutical composition according to any one of items 1-5, wherein the pharmaceutical composition is for use in treating scleroderma.

14. The pharmaceutical composition according to any one of items 1-13, wherein the pharmaceutical composition is administered intravenously.

The present invention is described by way of examples hereinafter.

EXAMPLES

1. Improvement of Fibrosis with Reovirus in Activated Hepatic Stellate Cells
(1) Experimental Methods Fibrosis involves production of large amounts of type I collagen from myofibroblasts, which are activated fibroblasts. Thus, human hepatic stellate cells (LX-2) were cultured with human transforming growth factor-β (TGF-β) (2 ng/ml) for 12 hours to be activated and to differentiate into myofibroblast-like cells. The activated human hepatic stellate cells were treated with reovirus (T3D) (alive virus) at an Multiplicity of Infection (MOI) 0, MOI 2.5, MOI 5, MOI 10, or MOI 20 in the presence of TGF-β (2 ng/ml). Control cells (MOCK) were cultured with normal medium in the presence of TGF-β (2 ng/ml). After 48 hours of the virus treatment, cell viabilities were measured by the alamarBlue assay, and total RNA was collected to determine expression levels of fibrosis marker genes by quantitative RT-PCR. The expression levels of fibrosis marker genes were determined in the virus-treated group at an MOI 20, and the cell viabilities were determined in the virus-treated groups at MOI 0, MOI 2.5, MOI 5, MOI 10, and MOI 20.

(2) Experimental Results

Figure 2:
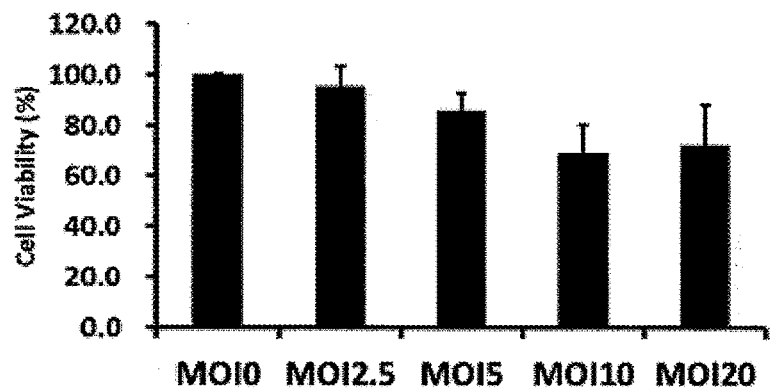
FIG. 2 shows cell viability of activated human hepatic stellate cells (LX-2) after treatment with reovirus (alive virus).

The expression levels of α-smooth muscle actin (α-SMA) and type I collagen as fibrosis markers were significantly low in the virus-treated group compared to the non-treated group (FIG. 1). No dramatic decreases in the cell viabilities were observed after 48 hours of the virus treatment (FIG. 2).

2. Improvement of Fibrosis with Reovirus in Activated Lung Fibroblasts
(1) Experimental Methods Human fetal lung fibroblasts (MRC-5) were treated in the same manner as described in Experiment 1. The expression levels of fibrosis marker genes were determined in the virus-treated group at an MOI 20, and the cell viabilities were determined in the virus-treated groups at MOI 20 and MOI 100.

(2) Experimental Results

Figure 3:
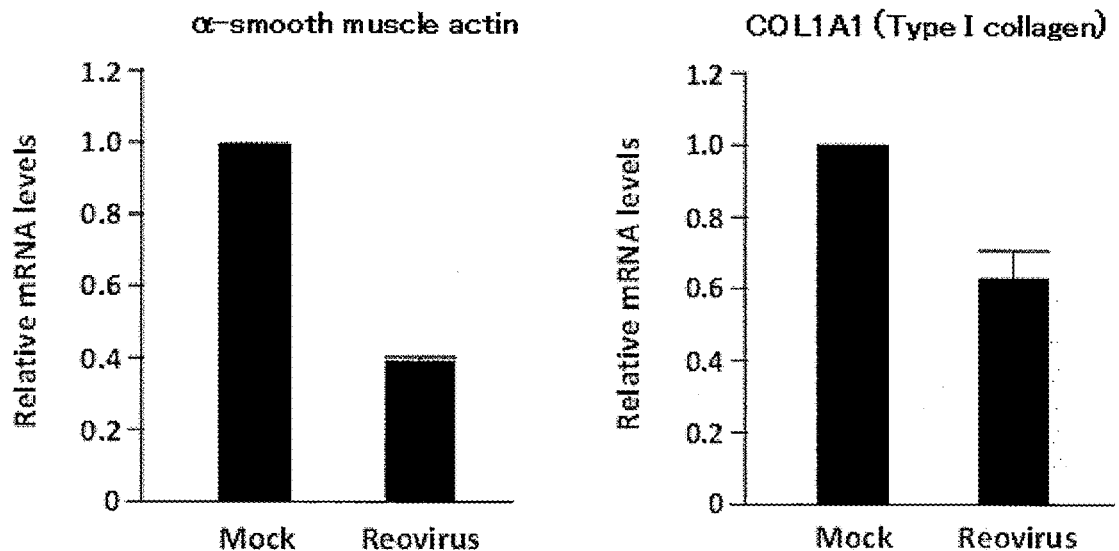
FIG. 3 shows expression of fibrosis markers in activated human lung fibroblasts (MRC-5).
Figure 4:
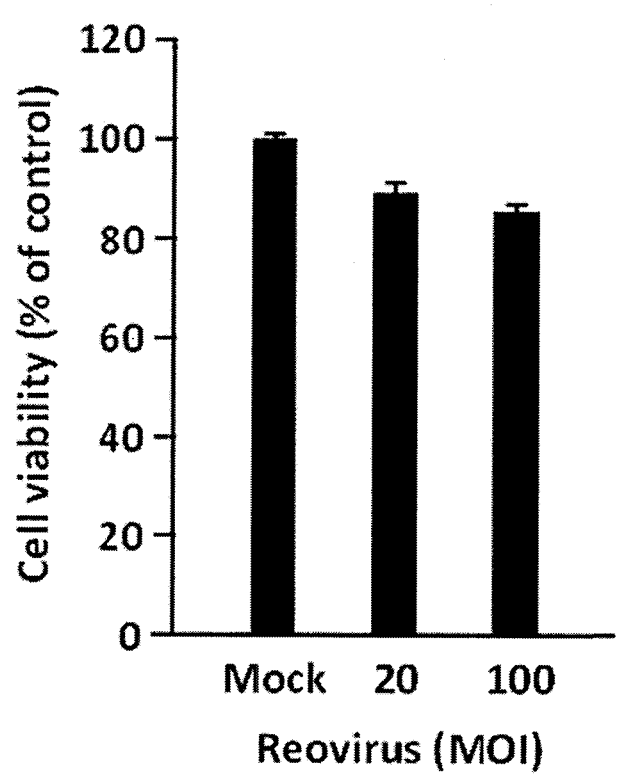
FIG. 4 shows cell viability of activated human lung fibroblasts (MRC-5) after treatment with reovirus (alive virus).

The expression levels of α-SMA and type I collagen as fibrosis markers were significantly low in the virus-treated group compared to the non-treated group (FIG. 3). No dramatic decreases in the cell viabilities were observed after 48 hours of the virus treatment (FIG. 4)

3. Improvement of Fibrosis with Reovirus in Mice having Carbon Tetrachloride-Induced Liver Fibrosis
(1) Experimental Methods C57Bl6 mice were treated with carbon tetrachloride at 0.6 ml/kg by intraperitoneal administration once a week for about 4 weeks and then twice a week for another about four weeks. Then, reovirus (T3D) (alive virus) was administered to the mice intravenously at 1×10$^8$ PFU/mouse. As a control (MOCK), PBS was administered. After the administration of reovirus, the mice were treated with carbon tetrachloride twice a week in the same manner as described above, and then opened followed by sacrifice to collect the liver. To evaluate the levels of liver fibrosis, total RNA was collected from the liver and expression levels of fibrosis marker genes were determined by quantitative RT-PCR. To evaluate expression levels of type I and type III collagens, tissue sections were prepared and stained with sirius red.

(2) Experimental Results

Figure 5:
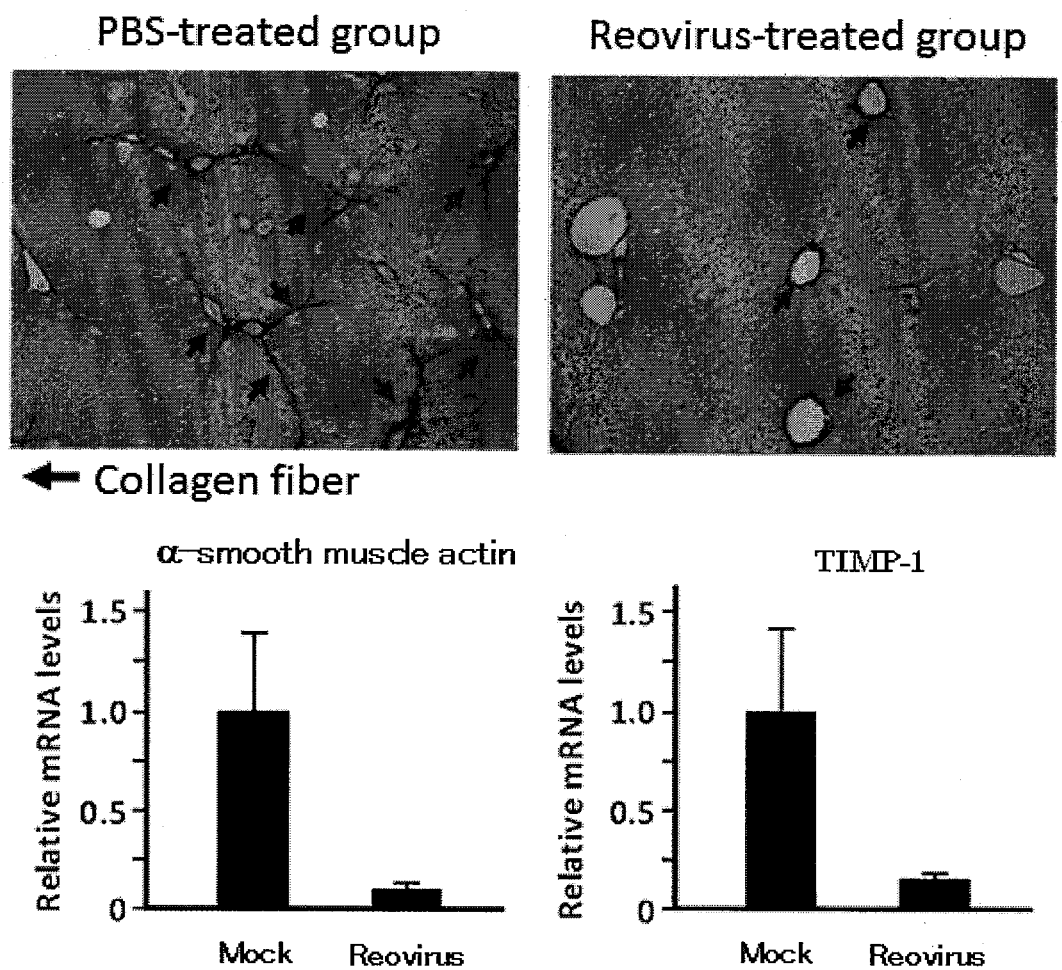
FIG. 5 shows improvement of fibrosis with reovirus (alive virus) in a mouse model of liver fibrosis. Arrows in the photograph indicate collagen fibers.

The expression levels of α-SMA and tissue inhibitor of metalloproteinase-1 (TIMP-1) as fibrosis markers were significantly decreased in the reovirus-treated group (FIG. 5, lower). The evaluation of the levels of liver fibrosis with tissue sections revealed that the amounts of type I and type III collagens were decreased (FIG. 5, upper).

4. Improvement of Fibrosis with Inactivated Reovirus in Mice having Carbon Tetrachloride-Induced Liver Fibrosis
(1) Experimental Methods C57 Bl6 mice were treated with carbon tetrachloride at 0.6 ml/kg by intraperitoneal administration twice a week for about 6 weeks. Then, reovirus (T3D) inactivated by ultraviolet (UV) irradiation (15 minutes) (confirmed as being inactivated) was administered intravenously at 1×10$^8$ PFU/mouse. As a control (MOCK), PBS was administered. After the administration of reovirus, the mice were treated with carbon tetrachloride twice a week in the same manner as described above, and then opened followed by sacrifice to collect the liver. To evaluate the levels of liver fibrosis, total RNA was collected from the liver and expression levels of fibrosis marker genes were determined by quantitative RT-PCR.

(2) Experimental Results

Figure 6:
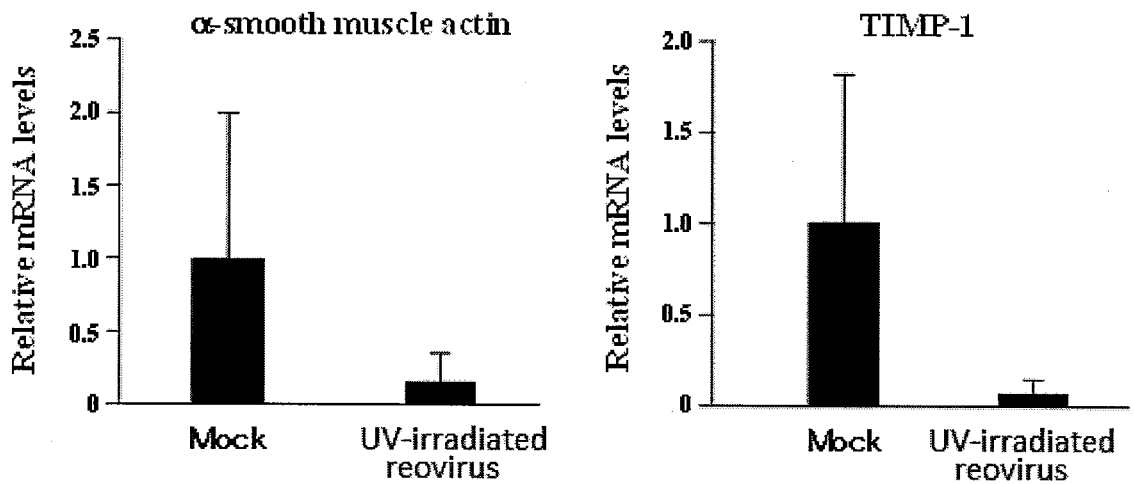
FIG. 6 shows improvement of fibrosis with reovirus (inactivated virus) in a mouse model of liver fibrosis.

The expression levels of α-SMA and TIMP-1 as fibrosis markers were decreased in the group treated with UV-irradiated reovirus compared to the mock-treated group (FIG. 6).

5. Improvement of Fibrosis with Reovirus in Activated Cardiac Fibroblasts
(1) Experimental Methods Fibroblasts were collected from the mouse heart and cultured for 96 hours in the presence of TGF-β (10 ng/ml) to be activated. The activated mouse cardiac fibroblasts were treated with reovirus (T3D) (alive virus) at an MOI 20 or MOI 100 in the presence of TGF-β (10 ng/ml). Control ibroblasts (MOCK) were cultured with normal medium in the presence of TGF-β (2 ng/ml). After 48 hours of the virus treatment, cell viabilities were measured by the alamarBlue assay, and total RNA was collected to determine expression levels of fibrosis marker genes by quantitative RT-PCR. The expression levels of fibrosis marker genes were determined in the virus-treated group at an MOI 100, and the cell viabilities were determined in the virus-treated groups at MOI 20 and MOI 100.

(2) Experimental Results

Figure 7:
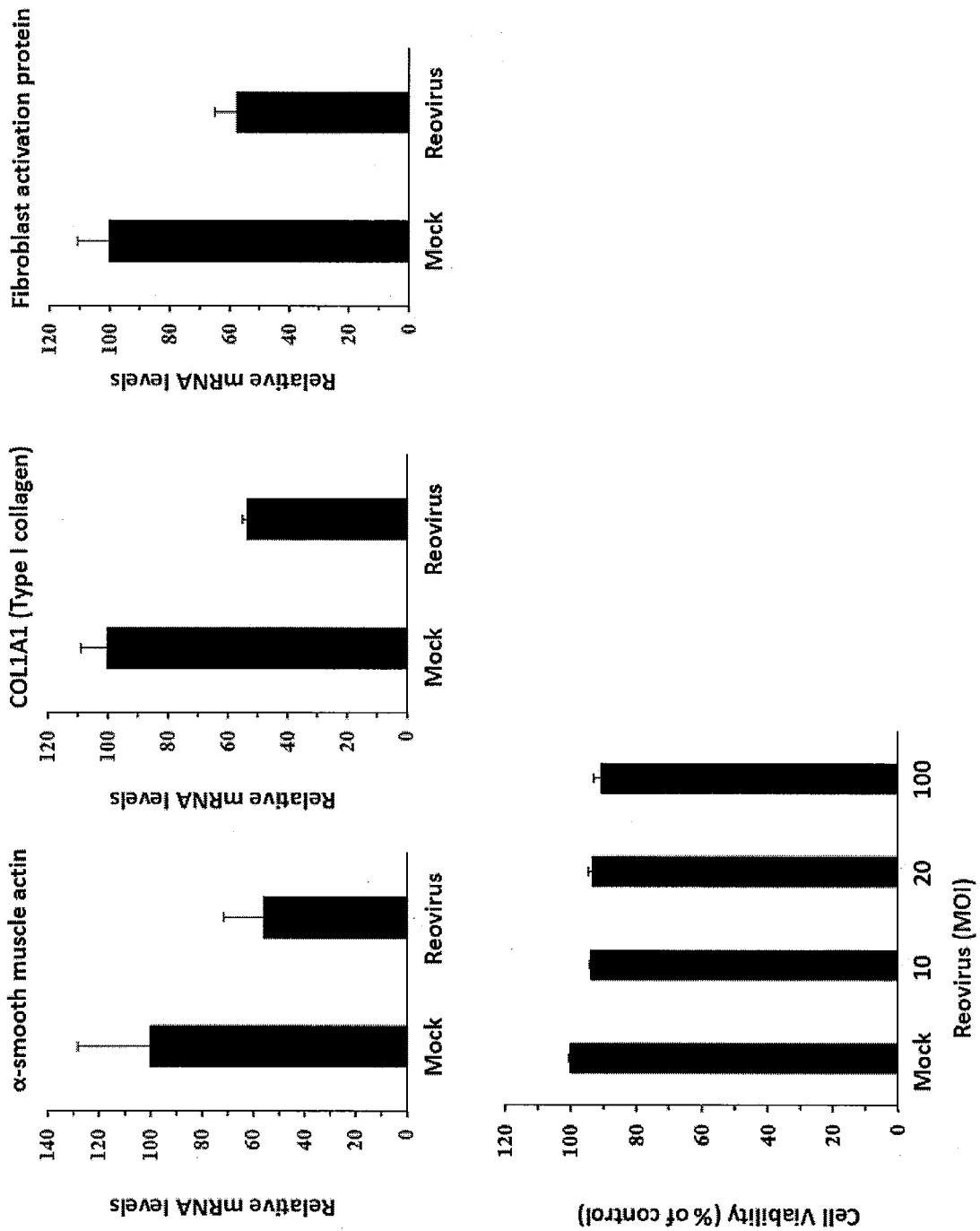
FIG. 7 shows expression of fibrosis markers in activated mouse cardiac fibroblasts and cell viability after treatment with reovirus (alive virus).

The expression levels of α-SMA, type I collagen, and fibroblast activation protein (FAP) as fibrosis markers were significantly low in the virus-treated group compared to the non-treated group (FIG. 7, upper). Decreases in the cell viabilities were not observed (FIG. 7, lower).

6. Improvement of Fibrosis with Reovirus in Activated Skin Fibroblasts
(1) Experimental Methods Primary human skin fibroblasts were cultured for 96 hours in the presence of TGF-β (10 ng/ml) to be activated. The activated human skin fibroblasts were treated with reovirus (T3D) (alive virus) at an MOT 20 or MOI 100 in the presence of TGF-β (10 ng/ml). Control fibroblasts (MOCK) were cultured with normal medium in the presence of TGF-β (10 ng/ml). After 0.48 hours of the virus treatment, cell viabilities were measured by the alamarBlue assay, and total RNA was collected to determine expression levels of fibrosis marker genes by quantitative RT-PCR. The expression levels of fibrosis marker genes were determined in the virus-treated group at an MOI 100, and the cell viabilities were determined in the virus-treated groups at MOI 20 and MOI 100.

(2) Experimental Results

Figure 8:
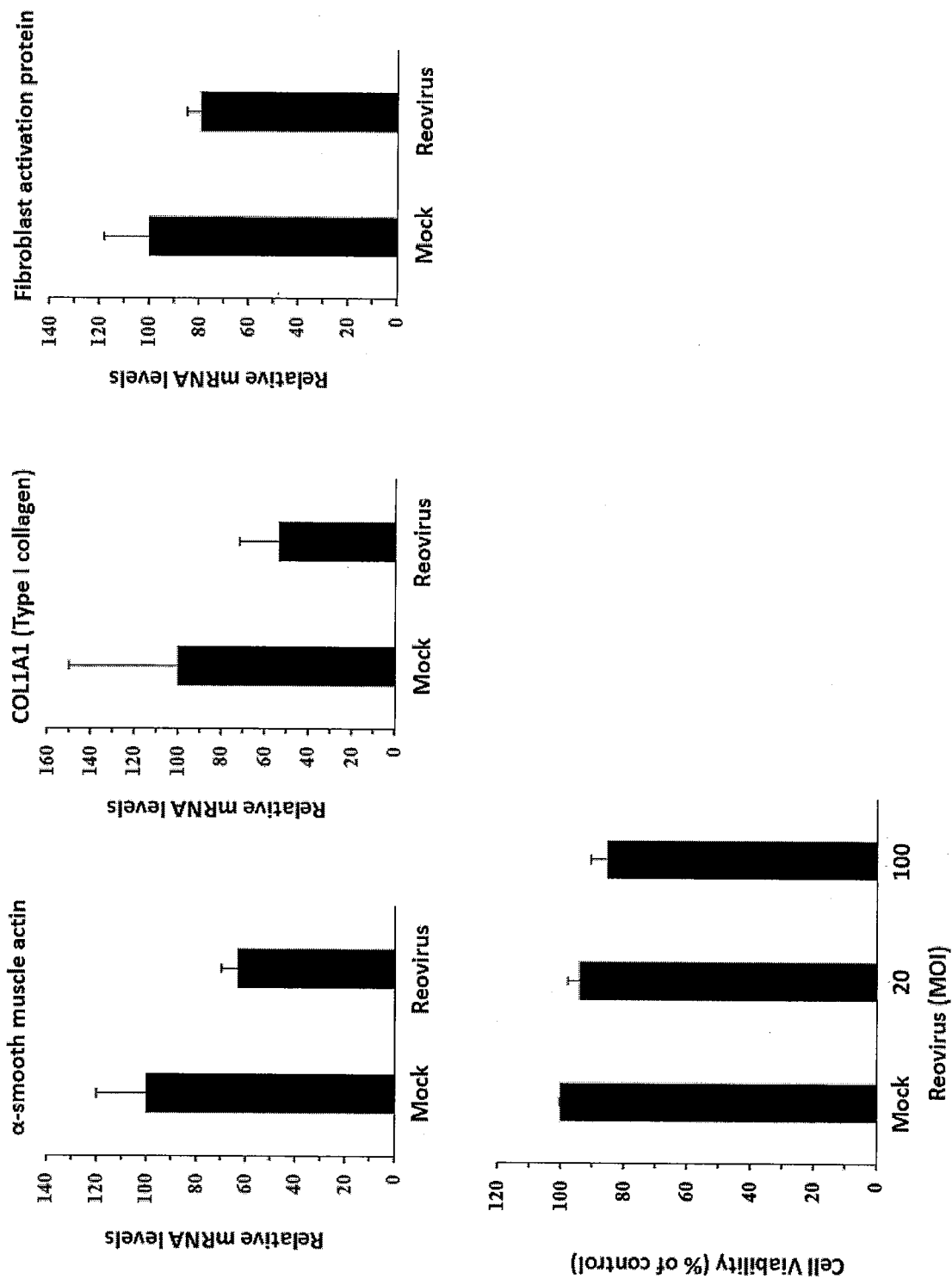
FIG. 8 shows expression of fibrosis markers in activated human skin fibroblasts and cell viability after treatment with reovirus (alive virus).

The expression levels of α-SMA, type I collagen, and FAP as fibrosis markers were significantly low in the virus-treated group compared to the non-treated group (FIG. 8, upper). No dramatic decreases in the cell viabilities were observed (FIG. 8, lower).

The invention claimed is:

1. A method for treating fibrosis in a human subject in need thereof, comprising administering a reovirus to the human subject, wherein the fibrosis is in an organ selected from liver, lung, heart and kidney, or the fibrosis is skin fibrosis, and the reovirus is strain Dearing of mammalian orthoreovirus type 3.

2. The method according to claim 1, wherein the reovirus is a live virus.

3. The method according to claim 1, wherein the reovirus is an inactivated virus.

4. The method according to claim 1, wherein the fibrosis is in an organ selected from liver, lung, heart, and kidney.

5. The method according to claim 1, wherein the fibrosis is in the liver, lung, or heart.

6. The method according to claim 1, wherein the fibrosis is in the liver or lung.

7. The method according to claim 1, wherein the human subject is suffering from a disease or a condition selected from liver fibrosis, liver cirrhosis, hepatitis B, hepatitis c, alcoholic hepatitis, non-alcoholic steatohepatitis, pulmonary fibrosis, cardiac fibrosis associated with myocardial infarction, and renal fibrosis associated with chronic renal disease.

8. The method according to claim 1, wherein the human subject is suffering from liver fibrosis, liver cirrhosis, hepatitis B, hepatitis c, alcoholic hepatitis, non-alcoholic steatohepatitis, or pulmonary fibrosis.

9. The method according to claim 1, wherein the human subject is suffering from cardiac fibrosis associated with myocardial infarction.

10. The method according to claim 1, wherein the fibrosis is skin fibrosis.

11. The method according to claim 1, wherein the human subject is suffering from scleroderma.

12. The method according to claim 1, wherein the reovirus is administered intravenously.

13. The method according to claim 1, wherein the fibrosis is in the liver.

14. The method according to claim 1, wherein the fibrosis is in the lung.

15. The method according to claim 1, wherein the fibrosis is in the heart.

16. The method according to claim 1, wherein the fibrosis is in the kidney.

17. A method for treating skin fibrosis in a human subject in need thereof, comprising administering a Dearing strain of mammalian orthoreovirus type 3 to the human subject.

* * * * *